United States Patent [19]
De Graaff et al.

[11] Patent Number: 5,763,260
[45] Date of Patent: Jun. 9, 1998

[54] METHOD TO ALTER THE PROPERTIES OF ACETYLATED XYLAN

[75] Inventors: Leendert H. De Graaff, Oosterbeek; Jacob Visser, Wageningen; Henriette C. Van Den Broeck, Ede, all of Netherlands; Francois Strozyk, Leforest, France; Felix J. M. Kormelink, Bennekom; Johannes C. P. Boonman, Haarlem, both of Netherlands

[73] Assignee: Gist-brocades, B.V., Netherlands

[21] Appl. No.: 401,136

[22] Filed: Mar. 8, 1995

Related U.S. Application Data

[62] Division of Ser. No. 851,976, Mar. 16, 1992, Pat. No. 5,426,043.

[30] Foreign Application Priority Data

Mar. 18, 1991 [EP] European Pat. Off. .............. 91200579

[51] Int. Cl.$^6$ .................. C12S 3/02; C12S 3/08; C12N 9/18; A23K 1/00
[52] U.S. Cl. .................. 435/274; 435/101; 435/197; 435/278; 426/53; 426/54; 426/635; 426/656
[58] Field of Search .................. 435/101, 197, 435/274, 278; 426/53, 54, 635, 656

[56] References Cited

PUBLICATIONS

Poutannen, K. and Puls, J., "The Xylanolytic Enzyme System of *Trichoderma reesei*," Chapter 46 in Lewis, N. and Paice, M., eds. *Biogenesis and Biodegradation of Plant Cell Wall Polymers*, American Cancer Society Symposium (1989) 399:630–640.

Grohmann, K. et al., "The Role of Ester Groups in Resistance of Plant Cell Wall Polysaccharides to Enzymatic Hydrolysis," *Applied Biochemistry and Biotechnology* (1989) Ref. 20/21:45–61.

Biely, P. et al., "Acetyl xylan esterases in fungal cellulolytic systems," *FEBS Letters* (1985) 186(1):80–84.

Poutanen, K. and Sundberg, M., "An acetyl esterase of *Trichoderma reesei* and its role in the hydrolysis of acetyl xylans," *Applied Microbiology and Biotechnology* (1988) 28:419–424.

Poutanen, K. et al., "Deacetylation of xylans by acetyl esterases of *Trichoderma reesei*," *Applied Microbiology and Biotechnology* (1990) 33:506–510.

Sundberg, M. and Poutanen, K., "Purification and Properties of Two Acetylxyan Esterases of *Trichoderma reesei*," *Biotechnology & Applied Biochemistry* (1991) 13(1):1–11.

Biely, P. et al., "Production of acetyl xylan esterase by *Trichoderma reesei* and *Schizophyllum commune*," *Canadian Journal of Microbiology* (1988) 34(6):767–772.

J.E. Morris et al., "The Fate of Acetyl Groups and Sugar Components During Digestion of Grass Walls in Sheep", Chem Absts. 87(25) 580, Absts. 87:199699, Dec. 1977.

*Primary Examiner*—Rebecca E. Prounty
*Attorney, Agent, or Firm*—Morrison & Foerster LLP

[57] ABSTRACT

Methods and DNA constructs are provided for the expression of a fungal acetyl xylan esterase gene in microbial hosts. A purified fungal acetyl xylan esterase is obtained which is suited for the use as an accessory enzyme in the degradation of acetylated xylans.

7 Claims, 2 Drawing Sheets

METHOD TO ALTER THE PROPERTIES OF ACETYLATED XYLAN

This application is a division of application Ser. No. 07/851,976 filed 16 Mar. 1992, now U.S. Pat. No. 5,426,043.

TECHNICAL FIELD

The present invention relates to the field of molecular biology. In particular, the invention relates to the cloning and expression of a DNA sequence encoding a fungal acetyl xylan esterase. The present invention provides a recombinant acetyl xylan esterase obtained by expression of the cloned DNA sequence encoding this protein. The protein thus obtained is used in xylan degradation in feed or pulp.

BACKGROUND OF THE INVENTION

The rigid structure of cell walls of plant tissues is due to xylans together with other hemicelluloses, pectins, cellulose and lignin. Xylans form the major hemicellulose, most xylans are heteropolysaccharides with a homopolymeric backbone chain of 1,4-linked β-D-xylopyranose units. The plant of origin determines the degree and the type of substitutions of the specific xylan. Xylans are found to contain many different side groups, among these L-arabinose, D-glucuronic acid or its 4-O-methyl ether, and acetic, p-coumaric, and ferulic acids are the most prominent.

It has been suggested that both acetyl and arabinosyl substituents increase the solubility of hemicellulose by decreasing the possibility of intermolecular aggregation, however, these substituents are at the same time a severe hindrance to the enzymatic degradation of the plant tissues. For example, it has been reported that acetylation inhibits the digestibility of plant polysaccharides in ruminants. Poutanen and Puls (1989) (In Biogenesis and Biodegradation of Plant Cell Wall Polymers (Lewis, N. and Paice, M. eds) ACS Symp. Ser. 399:630-640), have shown that the major xylanase of *Trichoderma reesei* is unable to depolymerize acetylated soluble xylan. Grohmann et al. (1989) (Appl. Biochem. Biotechnol. 20/21:45-61) have shown that after chemical deacetylation xylan is 5-7 times more digestible by ruminants.

Esterases (EC 3.1.1.6) are classified according to their substrate specificity. Since it is generally difficult to determine the natural substrate for these enzymes the classification is problematic and this problem is enlarged by the widespread appearence of esterases in nature. It is therefore not surprising that although the existence of enzymes that deacetylate xylan may have been anticipated in view of the long known occurrence of microbial esterases that were known to act on various synthetic substrates, it was not until recently that the existence of acetyl xylan esterases was demonstrated.

Biely et al. (1985, FEBS Lett. 186:80-84) demonstrated the presence of acetyl xylan esterases in (fungal) cellulolytic and hemicellulolytic systems: *Trichoderma reesei*, *Aspergillus nicer*, *Schizophyllum commune* and *Aureobasidium pullulans*. As compared with plant and animal esterases, these fungal esterases exhibit high specific activities towards acetylated glucuronoxylan and were therefore named acetyl xylan esterases.

Further investigations on the fungal acetyl esterases have been reported. Poutanen et al. (1988, Appl. Microbiol. Biotechnol. 28:419-425 and 1990, Appl. Microbiol. Biotechnol. 33:506-510) described the purification and characterization of acetyl xylan esterases from *T. reesei*. Enzymatic deacetylation of xylan using purified acetyl xylan esterase resulted in the precipitation of the remaining polymer structure. Due to this effect acetyl esterase is not used as a single first enzyme in the degradation of acetylated xylans. The highest xylose yield from acetylated xylan was obtained by the synergistic action of xylanase, β-xylosidase and acetyl xylan esterase.

To achieve a practically useful degradation of xylans there is a need for large amounts of the enzymes involved in the enzymatic hydrolysis of these highly substituted molecules. The present invention provides a way for obtaining large amounts of fungal acetyl xylan esterases, optionally in a purified form.

SUMMARY OF THE INVENTION

It is an object of the present invention to provide a purified and isolated acetyl xylan esterase of fungal origin. This protein is the expression product of the gene encoding a fungal acetyl xylan esterase.

The present invention further provides constructs for the microbial expression of the acetyl xylan esterase-encoding sequence using either its native regulatory sequences or, in an alternative embodiment, using the gene operatively coupled to regulatory regions such as promoter, secretion leader and terminator signals selected depending on the desired expression host.

It is a further object of the present invention to provide expression hosts, transformed with the expression constructs of the present invention, which are capable of the overexpression and, if desired, the secretion of the acetyl xylan esterase of fungal origin.

It is yet a further object of the present invention to provide methods for the production of large quantities of an acetyl xylan esterase.

Furthermore the present invention provides a method for increasing feed digestibility characterized in that an effective amount of acetyl xylan esterase is added to the feed. The present invention also provides a method for decreasing the viscosity of xylan containing compositions characterized in that an effective amount of acetyl xylan esterase is added.

The present invention also provides a method for the release of lignin from kraft pulp in the preparation of paper products.

DETAILED DESCRIPTION OF THE INVENTION

Figure 1:
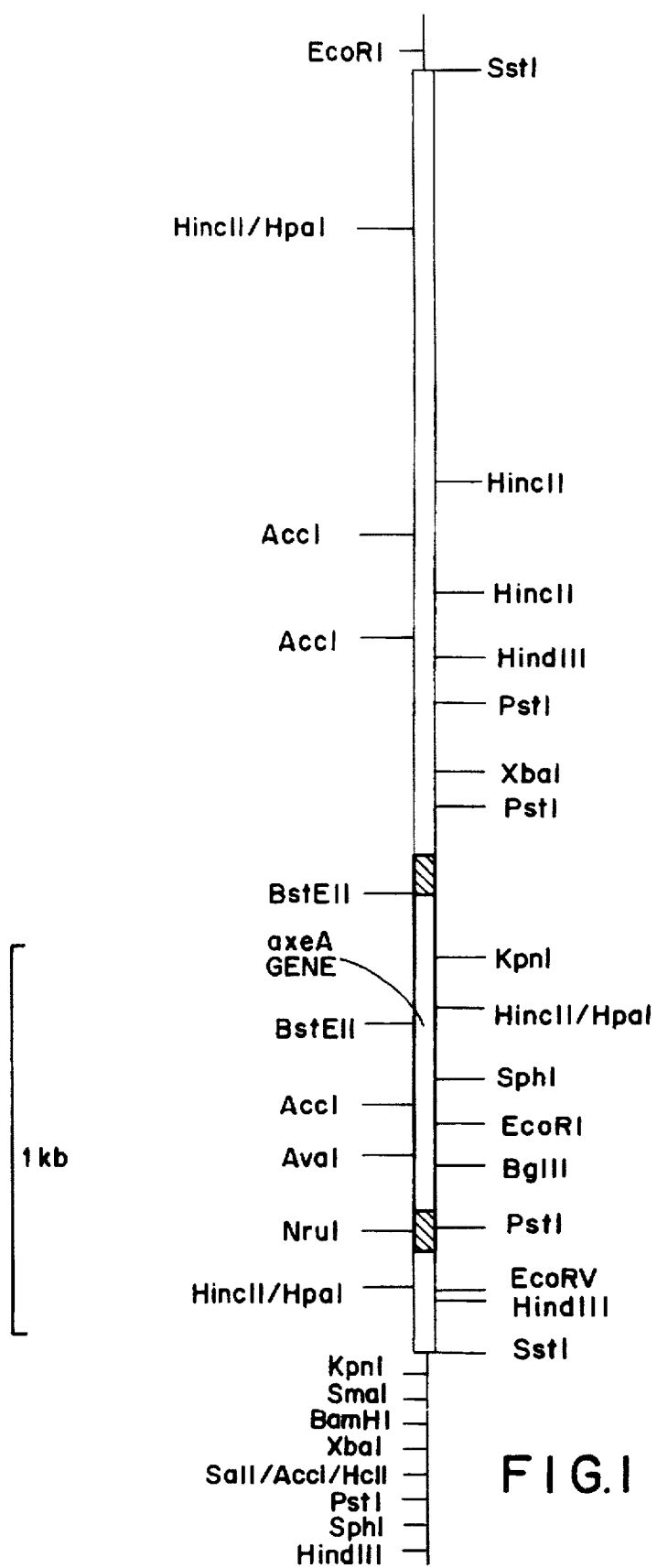
FIG. 1 shows the restriction map of a 3.4 kb Sst1 DNA fragment containing the *Aspergillus niger* axeA gene.

Filamentous fungi are widely known for their capacity to secrete large amounts of a variety of hydrolytic enzymes such as α-amylases, proteases and glucoamylases, and various plant cell wall degrading enzymes such as cellulases, hemicellulases, and pectinases.

The present invention describes a purified and isolated DNA molecule comprising the sequence of an acetyl xylan esterase gene of fungal origin and genetic variants thereof. Genetic variants are those DNA sequences encoding mutant acetyl xylan esterases. Also encompassed by the present invention are fungal DNA sequences that hybridize with the presented sequences under stringent conditions and that upon expression give rise to a protein which shows esterase activity. Specifically the *A. niger* acetyl xylan esteralse gene, isolated in one of the examples, was shown to hybridize with *T. reesei* chromosomal DNA.

The present invention also pertains to homologous or heterologous hosts transformed by recombinant DNA molecules containing the DNA sequences described above. With "homologous host" is intended the species from which the gene is obtained. "Heterologous host" pertains to hosts other than the source from which the gene is obtained. Heterologous hosts may be selected from bacteria, yeasts or fungi. The terms homologous and heterologous are also used with respect to the regulating sequences. In this case "homologous" refers to the regulating sequences which are native to the cloned gene and "heterologous" to regulating sequences from other genes or from the same gene obtained from another species.

Acetyl xylan esterases of particular interest are those which are obtained from fungi of the genera Asperqillus, Trichoderma, Schizophyllum. Preferred species are *Trichoderma reesei, Aspergillus nicer* and *Schizophyllum commune*.

Fungi showing acetyl xylan esterase activity can be used to isolate the protein by methods well-known in the art. In the presented examples *Aspergillus niger* is used as the source of the acetyl xylan esterase.

The acetyl xylan esterase is produced by culturing the Asperaillus strain. The protein is purified by known methods and the yield of the purification is followed by a suitable acivity assay.

As a first step of the characterisation of the protein structure a part of the amino acid sequence of the isolated protein is determined. When N-terminal amino acid sequencing techniques are used this can be the N-terminal part of the mature protein, but this can also be the N-terminus of an internal peptide obtained after digestion of the purified protein with a specific proteinase such as trypsin, chymotrypsin etc or with a chemical reagent e.g. CNBr. When using C-terminal sequencing methods it is possible to determine C-terminal sequences of the protein or peptides. Once such a sequence is known it is possible to derive a nucleotide probe based on this sequence. Preferably this probe is devised against a part of the protein which contains amino acids which are encoded by codons that show little degeneracy.

The probes that are obtained in such a way can be labeled and used to hybridize with the clones from a cDNA or genomic library. From the clones showing a positive hybridization signal the vector is isolated and the nucleotide sequence of the insert is determined. Hybridisation and sequencing can be repeated if no full length clone is found. Full-length clones can also be obtained by combining overlapping restriction fragments all encoding a part of the desired protein sequence. The obtained DNA sequence can be cloned in appropriate expression vectors. Where appropriate is related to the choice of the expression host organism. This cloning can also be performed without determination of the nucleotide sequence, however, this will probably give rise to a non-optimal construct. Preferred expression hosts can be bacteria, yeasts or fungi. Specifically Kluyveromyces, Bacillus, Aspergillus or *E. coli* are used.

To regulate the expression, regulatory regions are cloned in such a way that the gene is operationally linked with them. Among these regulatory regions homologous and heterologous promoters, operators, enhancers, signal sequences and ribosomal binding sites can be used. Furthermore, the gene can be cloned on a self-replicating vector or it can be integrated into the genome of the host organism, preferably more copies of the gene are used.

Finally, the obtained gene can in turn be used as a probe to hybridize with DNA libraries obtained from related species. Specifically the *A. niger* acetyl xylan eterase gene, isolated in one of the examples, was shown to hybridize with *T. reesei* chromosomal DNA.

In the examples the cloning and expression of a 3.4 kb Sstl DNA fragment obtained from *Aspergillus niger* is demonstrated. The expression is performed using the complete gene in *A. niger*.

As described above acetyl xylan esterase can be used to deeacetylate xylan. Since it was observed that the activity of acetyl xylan esterase as a single enzyme may lead to precipitation of the obtained polymer it is preferable to use the enzyme in conjunction with other xylan degrading enzymes such as xylanases, arabinofuranosidases, xylosidases and glucuronidases preferably selected from the group consisting of xylzanase, α-arabinofuranosidase, β-xylosidase and α-glucuronidase. In Example 5 the combined action of acetyl xylan esterase and β-(1,4)-xylanase and β-(1,4)-xylosidase respectively, is demonstrated.

Acetyl xylan esterases can preferably be used in processes wherein xylan has to be degraded. As a consequence of the deacylating reaction the xylan becomes better accessible for xylanases.

Specific applications of acetyl xylan esterases or combinations of this enzyme with other xylan degrading enzymes include;

the pretreatment of animal feed to increase the digestibility, addition of these enzymes to feed 'treatment in situ', treatment of fruit juices and beer in order to improve rheological characteristics and clarity, pulp and (waste-) paper processing in order to improve the process of bleaching and de-watering.

In general this enzyme or combinations of this enzyme with other enzymes can be used to degrade biological cell-wall material to increase digestibility or flow characteristics in industrial applications relating to the preparation of fruit juices or beer.

Another important aspect concerning the use of acetyl xylan esterase in feed is its effect on viscosity. Deacetylation of xylan decreases the solubility of the feed components and thereby the viscosity is diminished. This leads to an increased ease of handling, and a reduced anti-nutritional effect of the pentosanes. In accordance with this the present invention provides animal feed compositions containing acetyl xylan esterase.

Furthermore, the accesibility of xylan for xylanases is increased. This is important in the release of lignin from pulp. Generally kraft pulp is treated with xylanases in order to remove lignin in the preparation of paper products. Due to the high degree of acetylation of xylan xylanase is not optimally used. The effectivity of xylanases is greatly increased when pulp is treated with acetyl xylan esterase either before or at the same time as the xylanase treatment.

In accordance with the above the present invention provides a method for increasing feed digestibility characterized in that an effective amount of acetyl xylan esterase is added to the feed. The present invention also provides a method for decreasing the viscosity of xylan containing compositions characterized in that an effective amount of acetyl xylan esterase is added. The present invention also provides a method for the release of lignin from kraft pulp in the preparation of paper products.

The following examples are offered by way of illustration and are not meant to limit the scope of the present invention in any way.

EXPERIMENTAL

Buffers and stock solutions

Appropriate stock solutions were used in the experiments described in the examples.

The following stock solutions were made according to Maniatis et al. ('Molecular Cloning' Cold Spring Harbor, 1982 and 1989, 2nd ed.);

TE buffer, 20×SSC, Hybridization buffer, 100× Denhardt's solution, SM buffer, 50×TAE buffer, DNA loading buffer (xylene cyanol and bromophenol blue), NCZYM medium, LB medium. Ligation buffer was prepared as indicated by the supplier of the enzyme.

Further solutions contained the following components;
5×RNB per 1000 ml 121.10 g Tris, 73.04 g NaCl, 95.10 g EGTA, pH 8.5
Visniac solution 10 g EDTA, 4.4 g $ZnSO_4.7H_2O$, 1.0 g $MnCl_2.4H_2O$ 0.32 g $CoCl_2.6H_2O$, 0.32 g $CuSO_4 5H_2O$ 0.22 g $(NH_4)_6Mo_7O_{24}.4H_2O$, 1.47 g $CaCl_2.2H_2O$ 1.0 g $FeSO_4.7H_2O$, pH 4.0

(Visniac and Santer, 1957, Bact. Rev. 21:195–213)
Minimal medium per 1000 ml 6.0 g $NaNO_3$, 1.5 g $KH_2PO_4$, 0.5 g $MgSO_4.7H_2O$ 0.5 g KCl, 1 ml Visniac solution Carbon source as indicated, pH 6.0

Strains used in the Examples

*E. coli* JM101 (Yanisch-Perron et al., 1985, Gene 33:103)

*E. coli* LE 392 (Murray, 1977, Mol. Gen. Genet. 150:53–58)

*Asperqillus niger* N402 (Goosen et al., 1987, Curr. Genet. 11:499–503)

*Aspergillus niger* N593 (Goosen et al., 1987, supra)

Vectors used in the Examples pUC9 (Vieirra and Messing, 1982, Gene 19:259–268 and Yanisch-Perron et al., 1985)

M13mp18/M13mp19 (Messing, J., 1983, IOIC:10–78, Norrander et al., 1983, Gene 26:101–106)

Acetyl esterase assay

The assay was as described by Biely et al. (1985, supra). Enzyme solution (10–50 µl) was mixed with 1 ml of a freshly prepared saturated solution of 4-nitrophenyl acetate (SIGMA) in 0.2M phospate buffer, pH 6.5 and incubated at 22° C. Liberation of 4-nitrophenol was followed photometrically at 410 nm as a function of time. One unit of acetyl esterase activity hydrolyzes 1 µmole of the substrate in 1 min.

Enzymes

The endo-(1,4)-β-xylanase I, II, III (E.C. 3.2.1.8) and the β-(1,4)-xylosidase (E.C. 3.2.1.37) were purified as described by Kormelink et al. (1990, In: Proc. 5th European Congress on Biomass and Bioenergy, Lissabon 9–13 October 1989). from *Aspegillus awamori* CMI 142717.

Combined action of acetyl esterase and xylan-degrading enzymes

The release of acetic acid and xylose oligomers was determined by HPLC after degradation of steamed birchwood xylan by single or combined actions of acetyl esterase and endo-(1,4)-β-xylanase I, endo-(1,4)-β-xylanase II, endo-(1,4)-β-xylanase III and β-(1,4)-xylosidase. A 0.2% (w/v) steamed birchwood xylan solution was incubated with 1.0 µg/ml acetyl esterase and 0.1 µg/ml endo-(1,4)-β-xylanase I, endo(1,4)-β-xylanase II, endo-(1,4)-β-xylanase III or β-(1,4)xylosidase at 30° C. The degradation was followed over a time range from 0–8 hours. The reaction was terminated by placing the sample for 5 minutes in a boiling water bath. Steamed birchwood was prepared as described by Puls et al. (1985, Appl. Microbiol. Biotechnol. 22:416–423).

HPLC—Neutral sugars

Neutral sugars released by the single and combined action of endo-(1,4)-β-xylanase I, II, III, β-(1,4)-xylosidase and acetyl esterase on steamed birchwood xylan were determined by HPLC. Samples were pretreated with $Pb(NO_3)_2$ according to Voragenr et al. (1986, Food Hydrocolloids 1:65–70) and injected on a CH—Pb column (Merck, Darmstadt, FRG) eluted with millipore water (0.4 ml/min) at 85° C. Sugars were detected by a Shodex SE-61 RI detector.

EXAMPLES

Example 1

Purification and characterization of *A. niger* acetyl xylan esterase AXE I.

Example 1.1

Purification of *A. niger* acetyl xylan esterase AXE I

After growth of *Aspergillus niger* DS16813 the culture was centrifuged and the supernatant was concentrated through ultrafiltration. A sample of 73 ml was applied to a DEAE-trisacryl (IBF) column (a XK 50 Pharmacia column filled with 400 ml of DEAE-trisacryl and buffered with Tris-HCl 0.05M, pH 7.8) and eluted with a linear gradient 0.0–1.0M NaCl in Tris-HCl 0.05M, pH 7.8. Fractions were assayed for acetyl esterase activity, as described above.

Fractions containing acetyl esterase activity were pooled and applied to a semi-preparative DEAE HPLC column (Waters; DEAE 5 PW 21.5 mm×15 cm) equilibrated with phosphate 0.05M pH 7.5. Elution was with a linear 0.0–1.0M NaCl gradient in the same buffer. The final purification was performed with an analytical DEAE HPLC column (same as above but in this case 7.5 mm×7.5 cm) or using SDS-PAA gelelectrophoresis. The fractions obtained were used for amino acid sequencing as such or the protein was first digested with an appropriate proteolytic enzyme. In the latter case the peptides obtained were separated through HPLC, before amino acid sequencing was performed.

Example 1.2

Amino acid sequencing of N-terminal and internal peptides of acetyl xylan esterase Amino acid sequencing of the N-terminus of *A. niger* acetyl xylan esterase AXE I, using an Applied Biosystems gas phase sequencer, revealed the following sequence:

(SEQ ID NO:1)(Formula 1)

Amino acid sequence determination of CNBr peptides of acetyl xylan esterase AXE I, after separation using HPLC, revealed the following sequences:

CNBr peptide 1

(SEQ ID NO:2)(Formula 2)

CNBr peptide 2

(SEQ ID NO:3)(Formula 3)

Example 2

Screening of the *A. niger* genomic library for the acetyl xylan esterase gene (axeA) and isolation of the gene.

Example 2.1
$^{32}$P-labeling of synthetic oligonucleotides

The amino acid sequence shown in Example 1.2 (Formula 1) was used to derive oligonucleotide mixes corresponding to the N-terminal amino acid sequence. The oligonucleotides were synthesized by the phosphoamidite method described by Crea et al. (1979, Tetrahedron Lett. 5:395–398) using an Applied Biosystems oligonucleotide synthesizer.

The following oligonucleotide mixture was used;
(SEQ ID NO:4) 29 (Formula 4)
G G G G
in a final concentration of 37 pmol oligonucleotides per µl. This oligonucleotide mixture was labeled in a reaction mixture of the following composition; 37 pmol oligonucleotide mixture, 66 mM Tris.HCl pH 7.6, 1 mM ATP, 1 mM spermidine, 10 mM MgCl$_2$, 15 mM dithiothreitol, 200 µg/ml BSA, 34 pmol $\tau^{32}$-P ATP (NEN, 6000 Ci/mMol) and 30 U T$_4$ polynucleotide kinase (BRL) in a final volume of 50 µl. The reaction was terminated by the addition of 4 µl 0.5M EDTA pH 8.0. The labeled oligonucleotide mixture was used without further purification in screening of the genomic library (Example 2.3) and in Southern blottings (Example 2.5 and 2.6).

Example 2.2
Construction of a genomic library of *Aspergillus niger* strain DS16813 (CBS 323.90)

DNA from *Aspergillus niger* DS16813 (deposited at the Centraal Bureau voor Schimmelcultures, Baarn, The Netherlands on Jul. 20, 1990 (CBS 323.90)) was isolated using the procedure described by de Graaff et al. (1988, Curr. Genet. 13:315–321). Briefly, mycelium, grown overnight was harvested and stored at −80° C. Nucleic acids were isolated by disrupting 0.5 g frozen mycelium using an microdismembrator (Braun). The mycelial powder was extracted with extraction buffer containing:

1 ml tri-isopropylnaphtalene sulfonic acid (TNS) (20 mg/ml), 1 ml p-aminosalicylic acid (PAS) (120 mg/ml) and 0.5 ml 5×RNB buffer and which was equilibrated with 1.5 ml phenol. The extraction buffer was added to the mycelium powder and a phenol/chloroform, chloroform extraction was performed. The DNA was subsequently isolated by ethanol precipitation. RNA was removed from the solution by treating with RNase A.

DNA, isolated from *Aspergillus niger* DS16813, as described above, was partially digested by Sau 3A. The resulting fragments were size fractionated by electrophoresis on 0.4% agarose in TAE. Fragments of 14 kb to 22 kb in size, were recovered from the gel by cutting the appropriate region from the gel and subsequent electroelution.

The fragments were ligated with bacteriophage lambda EMBL 3 Bam HI arms, obtained from Promega, using a standard procedure. The ligated DNA was packaged in vitro using Gigapack II Gold packaging extract (Stratagene) and plated on *E. coli* LE392 using NZYCM medium according to the manufacturer's instructions.

The primary library thus obtained was titrated and amplified. A phage stock was made containing approximately $10^{10}$ pfu/ml.

Example 2.3
Screening of the *A. niger* genomic library for the axeA gene.

A genomic library of *A. niger* was constructed as described above. For obtaining the axeA gene, $3\times10^3$ pfu per plate are plated in NZYCM topagarose containing 0.7% agarose on four 85-mm-diameter NZYCM (1.2% agar) plates as described (Maniatis et al., 1982, supra, pp. 64), using *E. coli* LE392 as plating bacteria.

After overnight incubation of the plates at 37° C. two replicas of each plate were made on HybondN$^+$ filters (Amersham) as described in Maniatis et al. (1982, supra, pp. 320–321).

After wetting the filters in 3×SSC, the filters were washed for 60 min. at room temperature in 3×SSC. The filters were prehybridized at 65° C. for two buffer in prehybridization buffer containing; 6×SSC, 0.5% SDS, 10×Denhardt's solution and 100 µg/ml heat denatured herring sperm DNA (Boehringer Mannheim). After two hours of prehybridization the buffer was replaced by hybridization buffer which is identical to the prehybridization buffer, except that this buffer does not contain herring sperm DNA, but contains $^{32}$-P labeled oligonucleotide mix Formula 1, prepared as described in Example 2.1. The filters were hybridized for 18 hrs at a final temperature of 47° C., slowly reached from the initial temperature of 65° C.

After hybridization the filters were first washed in 2×SSC, after which the filters were washed in prewarmed hybridization buffer at 47° C. Finally the filters were washed twice for 30 min. at 56° C. in 6×SSC, 0.05% sodium pyrophosphate. The air dried filters were taped on a sheet of Whatman 3MM paper, keying marks were made with radioactive ink and the Whatman paper and filters covered with Saran Wrap. Hybridizing plaques were identified by exposure of Kodak XAR X-ray film for 72 hrs at −70° C. using an intensifying screen.

Seven hybridizing plaques, were identified and named lambda$_{axe1}$ to lambda$_{axe7}$. Each positive plaque was picked from the plate using a Pasteur pipette and the phages were eluted from the agar plug in 1 ml of SM buffer containing 20 µl chloroform, as described in Maniatis et al. (1982, supra, pp. 64). The phages obtained were purified by repeating the procedure described above using filter replicas from plates containing 50–100 plaques of the isolated phages.

After purification the phages were propagated by plating $5\times10^3$ phages on NZYCM medium. After overnight incubation at 37° C. confluent plates were obtained, from which the phages were eluted by adding 5 ml SM buffer and storing the plate for 2 hrs at 4° C. with intermittent shaking. After collection of the supernatant using a pipette, the bacteria were removed from the solution by centrifugation at 4,000×g for 10 min. at 4° C. To the supernatant 0.3% chloroform was added and the number of pfu determined. These phage stocks contain approximately $10^{10}$ pfu/ml.

Example 2.4
Isolation of DNA from bacteriophage lambda

Each of the isolated phages were propagated by combining $5*10^9$ *E. coli* LE392 bacteria in 300 µl SM buffer with $2*10^6$ pfu for 15 min. After incubation the infected bacteria were used to inoculate 100 ml prewarmed (37° C.) NZYCM medium and subsequently incubated for 9–12 hrs at 37° C. in a New Brunswick rotation shaker at 250 rpm, after which period the bacteria were lysed. The bacterial debris was removed by centrifugation for 10 min. at 10 krpm. at 4° C., in a Sorvall High Speed centrifuge. The phages were precipitated from the supernatant obtained (100 ml) by the addition of 10 g polyethyleneglycol-6000 and 11.7 g NaCl and storing the solution overnight at 4° C. The precipitated phages were collected by centrifugation at 14,000×g at 4° C. for 20 min. The supernatant was removed by aspiration, while the rest of the liquid was removed using a paper towel. The phages were carefully resuspended in 4 ml SM buffer and extracted once with an equal volume of chloroform.

Before the DNA was extracted from the phage particles, DNA and RNA originating from the lysed bacteria was removed by incubation of the phage suspension with DNase I and RNase A (both 100 µg/ml) for 30 min. at 37° C. The phage DNA was subsequently released from the phages by the addition of EDTA to a final concentration of 20 mM while the protein was removed from the solution by extracting twice with an equal volume phenol/chloroform/isoamyl alcohol (25:24:1). After separation of the phases by centrifugation using a Sorvall centrifuge (14,000×g, 10 min.), the aqueous phase was extracted once with an equal volume chloroform/isoamylalcohol (24:1). The phases were separated by centrifugation after which the DNA was precipitated from the aqueous phase by the addition 0.1 vol. 5M sodiumperchlorate and 0.1 vol. isopropanol and incubation on ice for 30 min. The DNA was recovered by centrifugation for 10 min. at 4° C. (14,000×g). The supernatant was removed by aspiration after which the DNA was resuspended in 400 µl TE buffer. The DNA was precipitated once again from this solution by the addition of 0.1 vol. 3M sodium acetate and 2 vol. ethanol. The DNA was collected by centrifugation for 10 min. at 4° C. (14,000×g). Tie supernatant was removed by aspiration, the remaining pellet was briefly dried under vacuum, after which the DNA was resuspended in 125 µl TE buffer containing 0.1 µg/ml RNase A. This purification procedure results in the isolation of approximately 50–100 µg DNA from each phage.

Example 2.5

Restriction analysis of axeA containing phages

The isolated DNA of phages lambda$_{axe1}$ to lambda$_{axe7}$ was analyzed by Southern analysis using the following restriction enzymes; EcoRI; HinDIII; SI and HinCII. The DNA was digested for 3 hrs at 37° C. in a reaction mixture composed of the following solutions; 5 µl (≈1 µg) DNA solution; 2 µl of the appropriate 10×Reaction buffer (BRL); 10 U Restriction enzyme (BRL) and sterile distilled water to give a final volume of 20 µl. After digestion the DNA was precipitated by the addition of 0.1 vol. 3M NaAc and 2 vol. ethanol. The DNA was collected by centrifugation for 10 min. at room temperature (14,000×g). The supernatant was removed by aspiration, the remaining pellet was briefly dried under vacuum and resuspended in sterile distilled water. After addition of 4 µl DNA loading buffer the samples were incubated for 10 min. at 65° C. and rapidly cooled on ice, before loading the samples on a 0.6% agarose gel in TAE buffer. The DNA fragments were separated by electrophoresis at 25 V for 15–18 hrs.

After electrophoresis the DNA was transferred and denatured by alkaline vacuum blotting (VacuGene XL, Pharmacia LKB) to nylon membrane (Gene Bind 45, Pharmacia LKB) as described in the instruction manual (pp. 25–26) and subsequently prehybridized and hybridized using the labeled oligonucleotide mixture Formula 1 as described in Example 2.1 and hybridization conditions as described in Example 2.2. The hybridization pattern was obtained by exposure of Kodak XAR-5 X-ray film for 18 hrs at −70° C. using an intensifying screen.

From the results obtained it is concluded that the DNA of five out of the seven isolated clones hybridize with the oligonucleotide mixture derived from the N-terminal amino acid sequence. In all five clones fragments originating from the same genomic region were found. In a more extensive Southern analysis, using the enzymes BglII, EcoRV, NcoI, PstI, SstI and XbaI, a partial restriction map of this genomic region was constructed. From this experiment it is concluded that a 3.4 kb SstI fragment contains the *A. niger* axeA gene.

Example 2.6

Subcloning of the *A. niger* axeA gene

From phage lambda$_{axe3}$ the 3.4 kb SstI fragment was isolated by digesting the phage DNA with SstI and separation of the fragments as described in Example 2.4. The fragment was cut from the agarose gel, after which it was recovered from the piece of agarose by electroelution using ISCO cups. Both on the large and the small container of this cup a dialysis membrane was mounted, the cup was filled with 0.005×TAE and the piece of agarose is placed in the large container of the cup. Subsequently the cup was placed in the electro-elution apparatus, with the large container in the cathode chamber containing TAE and the small container at the anode chamber containing TAE/3M Nacl. The fragments were electro-eluted at 100 V during 2 hrs. After this period the cup was taken from the electro-elution apparatus and the buffer was removed from the large container, while from the small container the buffer was only removed from the upper part. The remaining buffer (200 µl) containing the DNA fragments was dialyzed in the cup against distilled water during 30 min. Finally the DNA was precipitated by the addition of 0.1 vol. 3M NaAc, pH 5.6 and 2 vol. cold (−20° C.) ethanol. The DNA was collected by centrifugation (Eppendorf centrifuge) for 30 min. at 14,000×g. at 4° C. After removal of the supernatant the DNA pellet was dried using a Savant Speedvac vacuumcentrifuge. The DNA was dissolved in 10 µl TE buffer and the concentration determined by agarose electrophoresis, using Lambda DNA with a known concentration as a reference and ethidiumbromide staining to detect the DNA.

The fragment obtained was ligated in the vector pEMBL18 digested with SstI and dephosphorylated with alkaline phosphatase prepared as follows; 1 µl (1 µg/µl) pEMBL18 was mixed with 2 µl 10×React 10 (BRL), 1 µl (1 U/µl) SstI and 16 µl sterile distilled water. The DNA was digested for 1 hr at 37° C., after which 0.5 µl alkaline phosphatase (1 U/µl (Pharmacia LKB) was added followed by further incubation at 37° C. for another 30 min. The linearized vector was isolated from a 0.6% agarose gel as described above.

The 3.4 kb SstI fragment was ligated in the vector resulting in the plasmid pIM150, by the following procedure. 100 ng pEMBL18 fragment was mixed with 100 ng 3.4 kb SstI fragment and 4 µl 5*ligation buffer (composition; 500 mM Tris-HCl, pH 7.6; 100 mM MgCl$_2$; 10 mM ATP; 10 mM dithiotreitol; 25% PEG-6000) and 1 µl (1.2 U/µl) DNA ligase (BRL) was added to this mixture in a final volume of 20 µl. After incubation for 16 hrs at 14° C. the mixture was diluted to 100 µl with sterile water. 10 µl of the diluted mixture was used to transform *E. coli* JM101 competent cells, prepared by the CM1, CM2 method as described in the Pharmacia Manual for the M13 cloning/sequencing system. A selection of six of the resulting colonies were grown overnight in LB medium containing 100 µg/ml ampicillin. From the cultures plasmid DNA was isolated by the alkaline lysis method as described by *Maniatis* (et al. (1982, pp. 368–369), which was used in restriction analysis, as described in Example 2.4 to select a clone harboring the desired plasmid. Plasmid DNA was isolated on a large scale from 500 ml cultures *E. coli* JM101 containing the plasmid pIM150 grown in LB medium containing 100 µg/ml ampicillin (*Maniatis* et al., 1982, p 86). The plasmid was purified by CsCl centrifugation, phenolized, ethanol precipitated and dissolved in 400 µl TE. The yield was approximately 500 µg.

The plasmid pIM150 was further analyzed by restriction enzymes resulting in the restriction map shown in FIG. 1.

This plasmid was deposited with the Centraal Bureau voor Schimmelcultures (CBS) in Baarn, the Netherlands. In *E. coli* DH5α on Mar. 11 1991, under number CBS 157.91.

Example 3
Sequence determination of the *A. niger* axeA gene

The sequence of the *A. niger* axeA gene, its promoter-regulation region, the structural part of the gene and the termination region, was determined by subcloning fragments from pIM150 in M13mp18/mp19, in combination with the use of specific oligonucleotides as primers in the sequencing reactions.

For nucleotide sequence analysis restriction fragments were isolated as described in Example 2.5 and cloned in bacteriophage M13 mp18/19 RF DNA vectors (Messing, 1983, supra; Norrander et al., supra, 1983), digested with the appropriate restriction enzymes, as described in Example 2.5. The nucleotide sequences were determined by the dideoxynucleotide chain termination procedure (Sanger et al., 1977, Proc. Natl. Acad. Sci. USA 74:5463–5467) using the Pharmacia $T_7$ DNA polymerase sequencing kit. Computer analysis was done using the PC/GENE program. The sequence determined is given as SEQ ID NO:7 (in the Sequence Listing). The position of the introns was derived based on the consensus sequences for 5' and 3' splice sites.

Example 4
Expression of the cloned axeA gene in *A. niger* N593

Example 4.1
Introduction of the axea gene in *A. niger* N593 by cotransformation The plasmid pIM150, obtained in Example 2.5 was introduced in *A. niger* by cotransformation of *A. niger* N593 (a pyr mutant of *A. niger* N402) using the *A. niger* pyrA as a selective marker on the plasmid pGW635 (Goosen et al., 1989, Mol. Gen. Genet. 219:282–288) and the plasmid pIM150 as the cotransforming plasmid.

Protoplasts were prepared from mycelium by growing *A. niger* N593 on minimal medium supplemented with 0.5% yeast extract, 0.2% casamino acids, 50 mM glucose and 10 mM uridine for 20 hrs at 30° C. The preparation of protoplasts of *A. niger* N593 and the transformation procedure was performed as described by Goosen et al., 1987 (supra). The resulting PYR$^+$ transformants were analyzed for the expression of the axeA gene by Western blot analysis.

Example 4.2
Screening of transformants for the expression of the axeA gene

The transformants obtained in Example 4.1 were analyzed for the formation of the axeA gene product, the AXE I protein. Twenty transformants were selected and grown for 72 hrs on medium containing per 1; 30 g birch wood xylan (Roth); 6 g NaNO3, 0.5 g KCl, 0.5 g MgSO4.7H$_2$O, 0.5 g CaCl$_2$, 1.5 g KH2PO., and 0.1 g yeast extract and 1 ml/l Visniac solution (pH 6.0). After growth the mycelium was removed by filtration and the culture filtrate was analyzed by SDS-polyacrylamide gel electrophoresis, using a gel containing 12% acrylamide. The AXE I protein was detected on nitrocellulose after electroblotting and incubation with polyclonal antibodies raised against the AXE I protein purified as described in Example 1.1. The antibody bound, was detected after incubation with goat-anti-rabbit antibody conjugated to alkaline phosphatase, according to the Biorad instruction manual.

Four of the twenty transformants analyzed overproduced the AXE I protein as detected by this procedure. The protein was secreted into the medium. Of the transformants analyzed one was selected for giving the highest yields of the AXE I protein, transformant TrA10.

Figure 2:
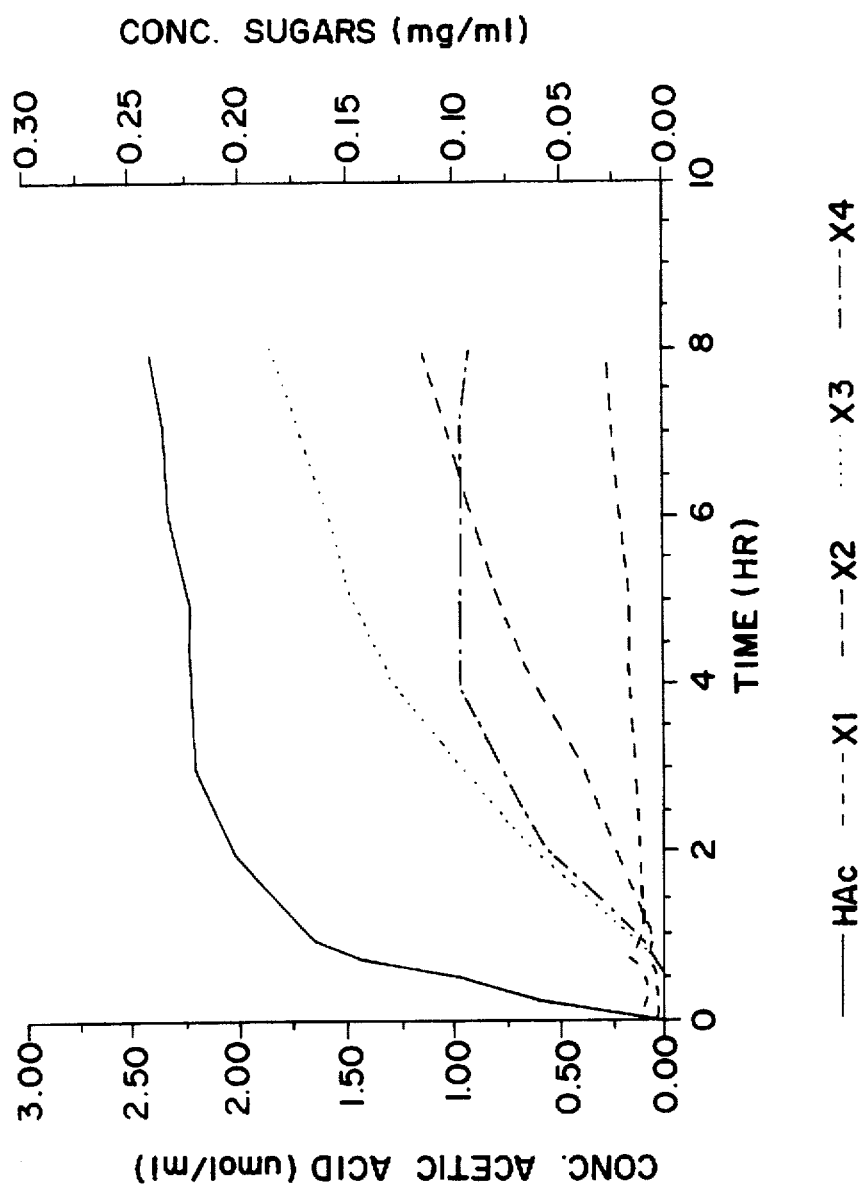
FIG. 2 shows the release of acetic acid (HAc) and xylose oligomers ($X_1$, $X_2$, $X_3$ and $X_4$) from a 0.2% (w/v) steamed birchwood xylan solution by the combined action of acetyl esterase (1 μg/ml) and endo-(1,4)-β-xylanase I (0.1 μg/ml).

Example 5
Combined action of acetyl xylan esterase and endo-(1,4)-β-xylanase and β-(1,4)-xylosidase respectively A 0.2% (w/v) steamed birchwood xylan solution was incubated with acetyl esterase and combinations of acetyl esterase and endo-(1,4)-β-xylanase I, endo-(1,4)-β-xylanase II, endo-(1,4)-β-xylanase III or β-(1,4)-xylosidase in time. Time curves (as shown for endo-(1,4)-β-xylanase in FIG. 2) show that endo-(1,4)-β-xylanase I, II and III start releasing significant amounts of xylose and xylose oligomers (X2, X3 and X4) only after most of the acetyl groups have been released. The acetyl esterase does not release more acetic acid than when used in combination with xylan-degrading enzymes. The release of xylose by β-(1,4)-xylosidase from steamed birchwood xylan is slowly but steady. Without acetyl xylan esterase, the endo-(1,4)-β-xylanases and the β-(1,4)-xylosidase do not degrade the steamed birchwood xylan i.e. they do not release significant amounts of X1, X2, X3 and X4. The acetyl groups may therefore block the enzyme activity of the endo-(1,4)-β-xylanases or β-(1,4)-xylosidase activity.

To emphasize the degradation of the steamed birchwood xylan, comparative studies were carried out by incubation of a steamed birchwood xylan for 24 hrs with only acetyl esterase, endo-(1,4)-β-xylanase I, endo-(1,4)-β-xylanase II, endo-(1,4)-β-xylanase III or β-(1,4)-xylosidase, and with combinations of acetyl esterase and these xylan-degrading enzymes. Also pre-incubations with acetyl esterase for 1 hr followed by 1 and 24 hrs incubations with the xylan-degrading enzymes were carried out. Table 1 shows the results of the release of acetic acid, xylose, and xylose oligomers after 24 hours of incubation.

The acetyl xylan esterase releases 2.60–2.80 and 4.30 μmol/ml of acetyl groups after 1 and 24 hrs respectively (4.30 μmol/ml equals 80–90% release of all the acetyl groups). There is no increase in the initial rate for the release of acetic acid by using the combination of xylan-degrading enzymes and acetyl xylan esterase.

Without acetyl xylan esterase, the endo-(1,4)-β-xylanases and β-(1,4)-xylosidase from *A. awamori* release no or only traces of xylose oligomers from steamed birchwood xylan (i.e. $X_1$ or $X_1$, $X_2$, and $X_3$, by β-(1,4)-xylosidase and endo-(1,4)-β-xylanase I respectively). In combination with acetyl xylan esterase, these xylan-degrading enzymes release reasonable amounts of xylose oligomers after 24 hrs of incubation. However, by pretreating the steamed birchwood xylan with acetyl esterase for only 1 hr, the amount of xylose oligomers is somewhat lower. The combination of acetyl xylan esterase and xylan-degrading enzymes thus releases the highest amount of $X_1$, $X_2$, $X_3$, and $X_4$. This discrepancy may be explained by a linearization of the xylose oligomers by deacylation of the steamed birchwood xylan. If not degraded into smaller oligomers by the xylan-degrading enzymes, the higher xylose oligomers may aggregate as a result of this linearization and cause a precipitate. This precipitate is less accessible for degradation (Poutanen et al, 1989 and 1990).

From the results presented here, it is clear that by the initial release of acetyl groups by the acetyl esterase, new sites have been created on the polysaccharide backbone suitable for the binding of endo-(1,4)-β-xylanase. The fact that the purified xylan-degrading enzymes from *A. awamori* did not degrade the steamed birchwood xylan significantly, coincides with the findings of Poutanen et al. (supra) that a crude preparation of *A. awamori* did not degrade steamed birchwood xylan significantly.

TABLE 1

Release of acetic acid, xylose and xylose oligomers from a 0.2% (w/v) steamed birchwood xylan solution by the single and combined action of 1.0 µg/ml acetyl esterase and 0.1 µg/ml endo-β-(1,4)-D-xylanase I, endo-β-(1,4)-D-xylanase II, endo-β-(1,4)-D-xylanase III or β-(1,4)-xylosidase.

| Type of incubation | Acetic acid[1] | Product formation | | | |
|---|---|---|---|---|---|
| | | $X^{2}$ | $X2^{2}$ | $X3^{2}$ | $X4^{2}$ |
| Blanc | 0.0 | 0.008 | 0.002 | 0.003 | 0.000 |
| AE | 4.30 | | | | |
| Endo I | 0.06 | 0.022 | 0.027 | 0.079 | 0.000 |
| Endo II | 0.12 | 0.010 | 0.011 | 0.011 | 0.000 |
| Endo III | 0.02 | 0.010 | 0.010 | 0.011 | 0.000 |
| β-xylosidase | 0.16 | 0.065 | 0.000 | 0.000 | 0.000 |
| AE + Endo I | 4.30 | 0.043 | 0.210 | 0.265 | 0.048 |
| AE + Endo II | 4.30 | 0.010 | 0.104 | 0.252 | 0.105 |
| AE + Endo III | 4.30 | 0.020 | 0.209 | 0.222 | 0.054 |
| AE + β-xylosidase | 4.30 | 0.237 | 0.006 | 0.007 | 0.006 |
| $AE^{3}$ + $Endo^{4}$ I | 2.64 | 0.036 | 0.149 | 0.253 | 0.063 |
| $AE^{3}$ + $Endo^{4}$ II | 2.76 | 0.010 | 0.038 | 0.080 | 0.045 |
| $AE^{3}$ + $Endo^{4}$ III | 2.55 | 0.012 | 0.067 | 0.077 | 0.042 |
| $AE^{3}$ + β-xylosidase[4] | 2.99 | 0.113 | 0.005 | 0.005 | 0.000 |

[1] µmol/ml
[2] mg/ml
[3] Pre-incubation 1 hr
[4] Pre-incubation 24 hrs

Example 6

In vitro test of acetyl xylan esterase activity under conditions simulating the digestive tract of poultry 1.1 grams of feed or feed components (with or without acetyl xylan esterase) was incubated for 1 hour in 50 mM sodium acetate buffer pH 5.5 at 39° C., simulating chicken's crop. After lowering the pH to 3.0 with HCl and addition of 5 ml of a pepsin solution (Merck: 5.28 g/l) the mixture was incubated for 1.5 hours at 39° C. as in the stomach. The small intestine of birds was simulated by raising the pH to 6.5 by the addition of sodium phosphate (2.5 ml 1M) and 2.5 ml pancrealine/bile acids. After another 1.5 hours incubation at 39° C. the mixture was centrifuged. The pellet was dried and its weight determined. The difference between the weights of the pellets of treated and untreated material was a measure for enzymatic activity under the standard conditions.

As examples of feed constituents wheat bran and maize meal were incubated with acetyl xylan esterase, according to the description given above. The dry matter digestibility was improved by several percents.

This indicates that acetyl xylan esterase can be used in the degradation of other than wood-borne hemicellulose material.

---

We claim:

1. A method to decrease the solubility of and to enhance the susceptibility to degradation of acetylated xylan which method comprises the steps of;
   i) culturing a microbial host modified to contain a DNA molecule, which DNA molecule comprises an expression system for a nucleotide sequence encoding a protein having acetyl xylan esterase activity, which encoding nucleotide sequence is operably linked to expression regulating sequences, wherein said encoding nucleotide sequence
   (a) encodes a protein which comprises the amino acid sequence shown as positions 26–304 in SEQ ID NO:8;
   (b) encodes a modified protein which differs by one or more amino acids from positions 26–304 of SEQ ID NO:8 having acetyl xylan esterase activity that is encoded by a nucleotide sequence which hybridizes with the nucleotide sequence of SEQ ID NO:7 under the hybridization conditions of a hybridization buffer which is 6×SSC, 0.5% SDS and 10×Denhardt's at a starting temperature of 65° C. and a final temperature of 47° C. followed by washing in 2×SSC, followed by washing in said hybridization buffer at 47° C., followed by two washes for 30 minutes at 56° C. in 6×SSC, 0.05% pyrophosphate:
   ii) isolating a protein having acetyl xylan esterase activity from said modified host; and
   iii) treating a composition containing said acetylated xylan with said isolated protein having acetyl xylan esterase activity.

2. The method of claim 1 which further includes treating said composition with a xylan degrading enzyme.

3. The method of claim 2 wherein said xylan-degrading enzyme is selected from the group consisting of a xylanase, an arabinofuranosidase, a xylosidase and a glucuronidase.

4. The method of claim 1 which results in a decrease in viscosity of said acetyl xylan-containing composition.

5. The method of claim 4 wherein said acetyl xylan-containing composition is an animal feed.

6. The method of claim 2 wherein said composition is a kraft pulp useful in the preparation of paper products, and said xylan degradation results in removal of lignins therefrom.

7. The method of claim 2 wherein said composition is an animal feed and said xylan degradation results in enhancing digestibility of said feed.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: Aspergillus niger ( x i ) SEQUENCE DESCRIPTION: SEQ ID NO:1:

```
Ser  Gly  Ser  Leu  Gln  Gln  Val  Thr  Asp  Phe  Gly  Asp  Asn  Pro  Thr  Asn
1                 5                             10                          15

Val  Gly  Met  Tyr  Ile
                20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( v i ) ORIGINAL SOURCE:
           ( A ) ORGANISM: Aspergillus niger ( x i ) SEQUENCE DESCRIPTION: SEQ ID NO:2:

Tyr Ile Tyr Val Pro Asn Asn Leu Ala Ser Asn Pro Gly Ile Val Val
1               5                   10                  15

Ala Ile His Tyr
            20

( 2 ) INFORMATION FOR SEQ ID NO:3:

( i ) SEQUENCE CHARACTERISTICS:
           ( A ) LENGTH: 20 amino acids
           ( B ) TYPE: amino acid
           ( C ) STRANDEDNESS: single
           ( D ) TOPOLOGY: linear ( i i ) MOLECULE TYPE: peptide ( v ) FRAGMENT TYPE: N-terminal ( v i ) ORIGINAL SOURCE:
           ( A ) ORGANISM: Aspergillus niger ( i x ) FEATURE:
           ( A ) NAME/KEY: Modified-site
           ( B ) LOCATION: 1
           ( D ) OTHER INFORMATION: /note= "This position is ?."

( i x ) FEATURE:
           ( A ) NAME/KEY: Modified-site
           ( B ) LOCATION: 11
           ( D ) OTHER INFORMATION: /note= "This position is
           ( H i s / T h r )."

( i x ) FEATURE:
           ( A ) NAME/KEY: Modified-site
           ( B ) LOCATION: 15
           ( D ) OTHER INFORMATION: /note= "X represents either
                   Histidine(His) or Threonine(Thr)"

( x i ) SEQUENCE DESCRIPTION: SEQ ID NO:3:

Xaa Ser Gly Tyr Ser Gly Ser Phe Pro Thr Xaa Gln Ile Tyr Xaa Ser
1               5                   10                  15

Gly Ser Ser Asp
            20

( 2 ) INFORMATION FOR SEQ ID NO:4:

( i ) SEQUENCE CHARACTERISTICS:
           ( A ) LENGTH: 29 base pairs
           ( B ) TYPE: nucleic acid
           ( C ) STRANDEDNESS: single
           ( D ) TOPOLOGY: linear ( i i ) MOLECULE TYPE: DNA (genomic)

( v i ) ORIGINAL SOURCE:
           ( A ) ORGANISM: Aspergillus niger ( i x ) FEATURE:
           ( A ) NAME/KEY: misc_feature
           ( B ) LOCATION: group(9, 18, 21)
           ( D ) OTHER INFORMATION: /note= "N represents the nucleotide
                   Inosine(I)"

( x i ) SEQUENCE DESCRIPTION: SEQ ID NO:4:

GGRTTRTCNC CRAARTCNGT NACCTGCTG                                29

( 2 ) INFORMATION FOR SEQ ID NO:5:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Aspergillus niger ( i x ) FEATURE:
      ( A ) NAME/KEY: misc_difference
      ( B ) LOCATION: group(9, 12)
      ( D ) OTHER INFORMATION: /note= "N represents the nucleotide
             Inosine(I)"

( x i ) SEQUENCE DESCRIPTION: SEQ ID NO:5:

CCRAARTCNG TNACYTGYTG                                                    20

( 2 ) INFORMATION FOR SEQ ID NO:6:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Aspergillus niger ( i x ) FEATURE:
      ( A ) NAME/KEY: misc_feature
      ( B ) LOCATION: group(6, 9)
      ( D ) OTHER INFORMATION: /note= "N represents the nucleotide
             Inosine(I)"

( x i ) SEQUENCE DESCRIPTION: SEQ ID NO:6:

TTRTTNGGNA CRTAKATRTA                                                    20

( 2 ) INFORMATION FOR SEQ ID NO:7:

( i ) SEQUENCE CHARACTERISTICS:
      ( A ) LENGTH: 1943 base pairs
      ( B ) TYPE: nucleic acid
      ( C ) STRANDEDNESS: single
      ( D ) TOPOLOGY: linear ( i i ) MOLECULE TYPE: DNA (genomic)

( v i ) ORIGINAL SOURCE:
      ( A ) ORGANISM: Aspergillus niger
      ( H ) CELL LINE: E. coli. JM101::pGW150

( i x ) FEATURE:
      ( A ) NAME/KEY: TATA_signal
      ( B ) LOCATION: 606..612

( i x ) FEATURE:
      ( A ) NAME/KEY: CAAT_signal
      ( B ) LOCATION: 534..538
      ( D ) OTHER INFORMATION: /note= "CCAAT box."

( i x ) FEATURE:
      ( A ) NAME/KEY: CDS
      ( B ) LOCATION: join(713..917, 971..1227, 1306..1755)

( i x ) FEATURE:
      ( A ) NAME/KEY: misc_feature
      ( B ) LOCATION: 713..787
      ( D ) OTHER INFORMATION: /note= "From 713 to 800 prepropeptide."

( i x ) FEATURE:
            ( A ) NAME/KEY: mat_peptide
            ( B ) LOCATION: join(788..917, 971..1227, 1306..1756)

( x i ) SEQUENCE DESCRIPTION: SEQ ID NO:7:

| | | | | | |
|---|---|---|---|---|---|
| AAATATGTCT | TTTATTACCT | TGTTCTGTTG | ACTGGTGCAT | TACTTAAAAC | TAGAACAGTT | 60 |
| GTTCAAACAC | AAGTTGGACC | TATACCTGTC | ATAACTCGCC | TCGTCGCGTT | ATTCATCATG | 120 |
| CAAAAACTAT | CCGTTATCAG | CGCCGGGAGT | ATACTCCCAA | GAAGCTCACT | CACATGCAAA | 180 |
| GAAATGTGCC | GATTGCTTAA | GCTTTACCCC | AGATTATTCC | GTAACCATAT | ATCCATTCTG | 240 |
| GCTGAATACC | GGCTATTTGA | TGCTGCATAC | TCTCACATTC | CGCACAGCCG | CCAGTGTGAA | 300 |
| GAATCACCAG | TGGTCCAGCC | CTGCAGTGGC | TCTAACGGGA | TCTGTTACGG | AGTTCGGCCC | 360 |
| GCAACGTCGA | TCTCTAACCA | TTTCGATCTG | GAGTTCCCAC | TCCGTGCCGT | CTATCCCAGA | 420 |
| CTCCTCATGT | CGGAGCTGTC | ACGGCTGTCA | CATTAGCCCT | GCTTAATTTC | CGTGATGAAA | 480 |
| TCAGCCTACA | CTGTCATTTC | TATGTCTAGA | CCACTGCCAA | ATACCCACTG | AACCCAATAC | 540 |
| TTCCACAAC | TATAGAAACA | TACTATTACT | CCATAATGTT | TCAATTTACC | CGCTCTCTGC | 600 |
| AGCGCTATAA | ATCGTCTTCA | AATCCTCTGG | CGTCTTTCCT | ACTGCCCAAG | CTGCATCTCT | 660 |
| TTTCACCTAG | CAGGATTCAA | GCGTAGTGCC | TAGCACGGCA | GAAGAAACCA | CC ATG | 715 |
| | | | | | Met | |
| | | | | | 1 | |

| | | | | | | | | | | | | | | | | |
|---|---|---|---|---|---|---|---|---|---|---|---|---|---|---|---|---|
| CTA | CTA | TCA | ACC | CAC | CTC | CTC | TTC | GTC | ATC | ACC | ACC | TTC | TTA | ACC | TCC | 763 |
| Leu | Leu | Ser | Thr | His | Leu | Leu | Phe | Val | Ile | Thr | Thr | Phe | Leu | Thr | Ser | |
| | | | 5 | | | | | 10 | | | | | 15 | | | |
| CTC | CTC | CAC | CCC | ATC | GCC | GCC | CAT | GCT | GTC | AAG | CGC | AGT | GGC | AGT | CTT | 811 |
| Leu | Leu | His | Pro | Ile | Ala | Ala | His | Ala | Val | Lys | Arg | Ser | Gly | Ser | Leu | |
| | | | 20 | | | | | 25 | | | | | 30 | | | |
| CAA | CAG | GTC | ACC | GAT | TTC | GGT | GAC | AAC | CCT | ACA | AAT | GTA | GGC | ATG | TAC | 859 |
| Gln | Gln | Val | Thr | Asp | Phe | Gly | Asp | Asn | Pro | Thr | Asn | Val | Gly | Met | Tyr | |
| | | | 35 | | | | | 40 | | | | | 45 | | | |
| ATC | TAC | GTG | CCT | AAC | AAC | TTG | GCC | TCA | AAT | CCA | GGT | ATC | GTG | GTT | GCA | 907 |
| Ile | Tyr | Val | Pro | Asn | Asn | Leu | Ala | Ser | Asn | Pro | Gly | Ile | Val | Val | Ala | |
| | | | 50 | | | | | 55 | | | | | 60 | | | 65 |
| ATC | CAC | TAC | T GTACGTTCCC | | CCACATTTCT | | ACAATATAAA | | CCACAATACT | | | | | | | 957 |
| Ile | His | Tyr | | | | | | | | | | | | | | |

| | | | | | | | | | | | | | | |
|---|---|---|---|---|---|---|---|---|---|---|---|---|---|---|
| AAGCATGGCA | TAG | GC ACC | GGT | ACC | GGC | CCC | GGC | TAC | TAC | AGC | GCC | TCC | | 1005 |
| | | Cys Thr | Gly | Thr | Gly | Pro | Gly | Tyr | Tyr | Ser | Ala | Ser | | |
| | | 70 | | | | | 75 | | | | | 80 | | |

| | | | | | | | | | | | | | | | | |
|---|---|---|---|---|---|---|---|---|---|---|---|---|---|---|---|---|
| CCC | TAC | GCC | ACC | CTC | TCC | GAG | CAA | TAC | GGC | TTT | ATC | GTG | ATC | TAC | CCG | 1053 |
| Pro | Tyr | Ala | Thr | Leu | Ser | Glu | Gln | Tyr | Gly | Phe | Ile | Val | Ile | Tyr | Pro | |
| | | | | 85 | | | | | 90 | | | | | 95 | | |
| TCC | AGC | CCA | TAC | TCC | GGT | GGC | TGT | TGG | GAC | GTG | AGT | TCA | CAG | GCA | ACG | 1101 |
| Ser | Ser | Pro | Tyr | Ser | Gly | Gly | Cys | Trp | Asp | Val | Ser | Ser | Gln | Ala | Thr | |
| | | | | 100 | | | | | 105 | | | | | 110 | | |
| TTA | ACA | CAC | AAC | GGG | GGC | GGA | AAC | AGT | AAC | TCC | ATT | GCC | AAC | ATG | GTC | 1149 |
| Leu | Thr | His | Asn | Gly | Gly | Gly | Asn | Ser | Asn | Ser | Ile | Ala | Asn | Met | Val | |
| | | | | 115 | | | | | 120 | | | | | 125 | | |
| ACC | TGG | ACG | ATT | AGC | GAG | TAC | GGG | GCC | GAT | AGT | AGC | AAG | GTG | TTC | GTG | 1197 |
| Thr | Trp | Thr | Ile | Ser | Glu | Tyr | Gly | Ala | Asp | Ser | Ser | Lys | Val | Phe | Val | |
| | | | | 130 | | | | | 135 | | | | | 140 | | |
| ACG | GGA | TCG | AGT | TCG | GGG | GCT | ATG | TTG | ACG | GTATTCCTC | | TTCCCTTCCA | | | | 1247 |
| Thr | Gly | Ser | Ser | Ser | Gly | Ala | Met | Leu | Thr | | | | | | | |
| 145 | | | | | 150 | | | | | | | | | | | |

| | | | | | |
|---|---|---|---|---|---|
| ACCGTTCCCC | CTCTCTACAA | ATTAAAATAG | TAAAAGTTGT | GCATGCTAAT | AAAATTAG | 1305 |

| | | | | | | | | | | | | | | | | |
|---|---|---|---|---|---|---|---|---|---|---|---|---|---|---|---|---|
| AAC | GTA | ATG | GCA | GCA | ACC | TAC | CCC | GAA | CTC | TTC | GCC | GCC | GCC | ACC | GTC | 1353 |

```
Asn  Val  Met  Ala  Ala  Thr  Tyr  Pro  Glu  Leu  Phe  Ala  Ala  Ala  Thr  Val
155                 160                      165                      170

TAC  TCC  GGA  GTC  TCA  GCC  GGG  TGC  TTC  TAC  TCG  AAC  ACC  AAC  CAA  GTA     1401
Tyr  Ser  Gly  Val  Ser  Ala  Gly  Cys  Phe  Tyr  Ser  Asn  Thr  Asn  Gln  Val
                    175                      180                      185

GAT  GGA  TGG  AAT  TCC  ACT  TGC  GCC  CAG  GGT  GAT  GTA  ATC  ACC  ACC  CCC     1449
Asp  Gly  Trp  Asn  Ser  Thr  Cys  Ala  Gln  Gly  Asp  Val  Ile  Thr  Thr  Pro
               190                      195                      200

GAG  CAC  TGG  GCC  AGT  ATT  GCA  GAG  GCA  ATG  TAC  TCG  GGA  TAC  TCA  GGA     1497
Glu  His  Trp  Ala  Ser  Ile  Ala  Glu  Ala  Met  Tyr  Ser  Gly  Tyr  Ser  Gly
          205                      210                      215

AGT  CGT  CCA  AGG  ATG  CAG  ATC  TAC  CAC  GGT  ACT  CTC  CAT  ACG  ACG  CTG     1545
Ser  Arg  Pro  Arg  Met  Gln  Ile  Tyr  His  Gly  Thr  Leu  His  Thr  Thr  Leu
     220                      225                      230

TAT  CCT  CAG  AAC  TAC  TAT  GAG  ACG  TGC  AAG  CAG  TGG  TCT  GGA  GTG  TTT     1593
Tyr  Pro  Gln  Asn  Tyr  Tyr  Glu  Thr  Cys  Lys  Gln  Trp  Ser  Gly  Val  Phe
235                      240                      245                      250

GGA  TAT  GAT  TAT  AGC  GCA  CCG  GAG  AAG  ACG  GAG  GCG  AAT  ACC  CCA  CAG     1641
Gly  Tyr  Asp  Tyr  Ser  Ala  Pro  Glu  Lys  Thr  Glu  Ala  Asn  Thr  Pro  Gln
                    255                      260                      265

ACG  AAT  TAC  GAG  ACG  ACG  ATT  TGG  GGA  GAT  AGT  CTG  CAG  GGA  ATC  TTC     1689
Thr  Asn  Tyr  Glu  Thr  Thr  Ile  Trp  Gly  Asp  Ser  Leu  Gln  Gly  Ile  Phe
               270                      275                      280

GCG  ACA  GGC  GTG  GGT  CAT  ACG  GTG  CCG  ATT  CAT  GGG  GAT  AAG  GAT  ATG     1737
Ala  Thr  Gly  Val  Gly  His  Thr  Val  Pro  Ile  His  Gly  Asp  Lys  Asp  Met
          285                      290                      295

GAG  TGG  TTT  GGG  TTT  GCT  TGATTGGATG ATCGAATGGT TTAGCCTGGG                     1785
Glu  Trp  Phe  Gly  Phe  Ala
300

GGTATCTCGG AACCGGGAAT GATGAAACTT CTGAAGTATG ATATGTTAAC GATATCGCGT                  1845

CAACGAGCGT TTGTTGAAGC TTTAGTGTGT AATGTGGAGT ATGAGCAAAA TGTGCGCTGC                  1905

CCGTGTCTGA TGCCAAAACC AATGCAGCAC AAGAGCTC                                          1943
```

( 2 ) INFORMATION FOR SEQ ID NO:8:

( i ) SEQUENCE CHARACTERISTICS:
        ( A ) LENGTH: 304 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Leu  Leu  Ser  Thr  His  Leu  Leu  Phe  Val  Ile  Thr  Thr  Phe  Leu  Thr
1                   5                        10                       15

Ser  Leu  Leu  His  Pro  Ile  Ala  Ala  His  Ala  Val  Lys  Arg  Ser  Gly  Ser
               20                       25                       30

Leu  Gln  Gln  Val  Thr  Asp  Phe  Gly  Asp  Asn  Pro  Thr  Asn  Val  Gly  Met
          35                       40                       45

Tyr  Ile  Tyr  Val  Pro  Asn  Asn  Leu  Ala  Ser  Asn  Pro  Gly  Ile  Val  Val
     50                       55                       60

Ala  Ile  His  Tyr  Cys  Thr  Gly  Thr  Gly  Pro  Gly  Tyr  Tyr  Ser  Ala  Ser
65                       70                       75                       80

Pro  Tyr  Ala  Thr  Leu  Ser  Glu  Gln  Tyr  Gly  Phe  Ile  Val  Ile  Tyr  Pro
               85                       90                       95

Ser  Ser  Pro  Tyr  Ser  Gly  Gly  Cys  Trp  Asp  Val  Ser  Ser  Gln  Ala  Thr
          100                      105                      110

Leu  Thr  His  Asn  Gly  Gly  Gly  Asn  Ser  Asn  Ser  Ile  Ala  Asn  Met  Val
     115                      120                      125
```

| Thr | Trp | Thr | Ile | Ser | Glu | Tyr | Gly | Ala | Asp | Ser | Ser | Lys | Val | Phe | Val |
|---|---|---|---|---|---|---|---|---|---|---|---|---|---|---|---|
| | 130 | | | | | 135 | | | | | 140 | | | | |
| Thr | Gly | Ser | Ser | Ser | Gly | Ala | Met | Leu | Thr | Asn | Val | Met | Ala | Ala | Thr |
| 145 | | | | | 150 | | | | | 155 | | | | | 160 |
| Tyr | Pro | Glu | Leu | Phe | Ala | Ala | Ala | Thr | Val | Tyr | Ser | Gly | Val | Ser | Ala |
| | | | | 165 | | | | | 170 | | | | | 175 | |
| Gly | Cys | Phe | Tyr | Ser | Asn | Thr | Asn | Gln | Val | Asp | Gly | Trp | Asn | Ser | Thr |
| | | | 180 | | | | | 185 | | | | | 190 | | |
| Cys | Ala | Gln | Gly | Asp | Val | Ile | Thr | Thr | Pro | Glu | His | Trp | Ala | Ser | Ile |
| | | 195 | | | | | 200 | | | | | 205 | | | |
| Ala | Glu | Ala | Met | Tyr | Ser | Gly | Tyr | Ser | Gly | Ser | Arg | Pro | Arg | Met | Gln |
| | 210 | | | | | 215 | | | | | 220 | | | | |
| Ile | Tyr | His | Gly | Thr | Leu | His | Thr | Thr | Leu | Tyr | Pro | Gln | Asn | Tyr | Tyr |
| 225 | | | | | 230 | | | | | 235 | | | | | 240 |
| Glu | Thr | Cys | Lys | Gln | Trp | Ser | Gly | Val | Phe | Gly | Tyr | Asp | Tyr | Ser | Ala |
| | | | | 245 | | | | | 250 | | | | | 255 | |
| Pro | Glu | Lys | Thr | Glu | Ala | Asn | Thr | Pro | Gln | Thr | Asn | Tyr | Glu | Thr | Thr |
| | | | 260 | | | | | 265 | | | | | 270 | | |
| Ile | Trp | Gly | Asp | Ser | Leu | Gln | Gly | Ile | Phe | Ala | Thr | Gly | Val | Gly | His |
| | | 275 | | | | | 280 | | | | | 285 | | | |
| Thr | Val | Pro | Ile | His | Gly | Asp | Lys | Asp | Met | Glu | Trp | Phe | Gly | Phe | Ala |
| | 290 | | | | | 295 | | | | | 300 | | | | |